United States Patent
Brown

(10) Patent No.: US 11,193,918 B2
(45) Date of Patent: Dec. 7, 2021

(54) VEHICULAR CARBON MONOXIDE ALARM

(71) Applicant: Michelle Brown, Brooklyn, NY (US)

(72) Inventor: Michelle Brown, Brooklyn, NY (US)

( * ) Notice: Subject to any disclaimer, the term of this patent is extended or adjusted under 35 U.S.C. 154(b) by 149 days.

(21) Appl. No.: 16/674,147

(22) Filed: Nov. 5, 2019

(65) Prior Publication Data
US 2021/0132021 A1    May 6, 2021

(51) Int. Cl.
*G01N 33/00* (2006.01)
*B60Q 5/00* (2006.01)
*B60Q 9/00* (2006.01)
*B63B 43/00* (2006.01)

(52) U.S. Cl.
CPC ......... *G01N 33/0063* (2013.01); *B60Q 5/005* (2013.01); *B60Q 9/00* (2013.01); *G01N 33/004* (2013.01); *G01N 33/0047* (2013.01); *B63B 43/00* (2013.01)

(58) Field of Classification Search
CPC .......... G01N 33/0063; G01N 33/0047; G01N 33/004; B60Q 9/00; B60Q 5/005
See application file for complete search history.

(56) References Cited

U.S. PATENT DOCUMENTS

| | | | |
|---|---|---|---|
| 4,443,793 A * | 4/1984 | Hall, Jr. ............... | G08B 17/117 |
| | | | 340/634 |
| D391,214 S | 2/1998 | Hook | |
| 6,154,130 A * | 11/2000 | Mondejar ............. | G08B 13/08 |
| | | | 340/321 |
| 7,683,768 B2 | 3/2010 | Lindahl | |
| 8,803,677 B1 | 8/2014 | Miller | |
| 9,194,358 B1 | 11/2015 | Avramidis | |
| 9,196,146 B1 | 11/2015 | Vincente | |
| 9,803,412 B1 | 10/2017 | Fontanini | |
| 2002/0171544 A1 * | 11/2002 | Schmurr ............... | G08B 25/04 |
| | | | 340/538 |
| 2015/0097663 A1 * | 4/2015 | Sloo ...................... | G06T 7/70 |
| | | | 340/501 |
| 2017/0335781 A1 | 11/2017 | Augusty | |
| 2018/0345859 A1 * | 12/2018 | Zehr ..................... | G08B 21/14 |
| 2021/0016624 A1 * | 1/2021 | Gilgeours ............. | B60H 1/008 |

FOREIGN PATENT DOCUMENTS

WO        0137231        5/2001

* cited by examiner

*Primary Examiner* — Hongmin Fan

(57) ABSTRACT

The vehicular carbon monoxide and volatile organic compounds alarm is configured for use with a vehicle. The vehicle is further defined with a passenger space. The vehicular carbon monoxide and volatile organic compounds alarm is maintained in the passenger space of the vehicle. The vehicular carbon monoxide and volatile organic compounds alarm is a sensor. The vehicular carbon monoxide and volatile organic compounds alarm monitors the concentration of carbon monoxide and volatile organic compounds in the air in the passenger space of the vehicle. The vehicular carbon monoxide and volatile organic compounds alarm generates a visible and audible alarm when the concentration of carbon monoxide and volatile organic compounds in the passenger space of the vehicle exceeds a predetermined level. The vehicular carbon monoxide and volatile organic compounds alarm comprises an operating circuit and a housing. The housing contains the operating circuit.

17 Claims, 7 Drawing Sheets

VEHICULAR CARBON MONOXIDE ALARM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of physics and signaling including alarm systems, more specifically, a toxic gas alarm. (G08B21/14)

SUMMARY OF INVENTION

The vehicular carbon monoxide and volatile organic compounds alarm is configured for use with a vehicle. The vehicle is further defined with a passenger space. The vehicular carbon monoxide and volatile organic compounds alarm is maintained in the passenger space of the vehicle. The vehicular carbon monoxide and volatile organic compounds alarm is a sensor. The vehicular carbon monoxide and volatile organic compounds alarm monitors the concentration of carbon monoxide and volatile organic compounds in the air in the passenger space of the vehicle. The vehicular carbon monoxide and volatile organic compounds alarm generates a visible and audible alarm when the concentration of carbon monoxide and volatile organic compounds in the passenger space of the vehicle exceeds a predetermined level. The vehicular carbon monoxide and volatile organic compounds alarm comprises an operating circuit and a housing. The housing contains the operating circuit.

These together with additional objects, features and advantages of the vehicular carbon monoxide and volatile organic compounds alarm will be readily apparent to those of ordinary skill in the art upon reading the following detailed description of the presently preferred, but nonetheless illustrative, embodiments when taken in conjunction with the accompanying drawings.

In this respect, before explaining the current embodiments of the vehicular carbon monoxide and volatile organic compounds alarm in detail, it is to be understood that the vehicular carbon monoxide and volatile organic compounds alarm is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the vehicular carbon monoxide and volatile organic compounds alarm.

It is therefore important that the claims be regarded as including such equivalent construction insofar as they do not depart from the spirit and scope of the vehicular carbon monoxide and volatile organic compounds alarm. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
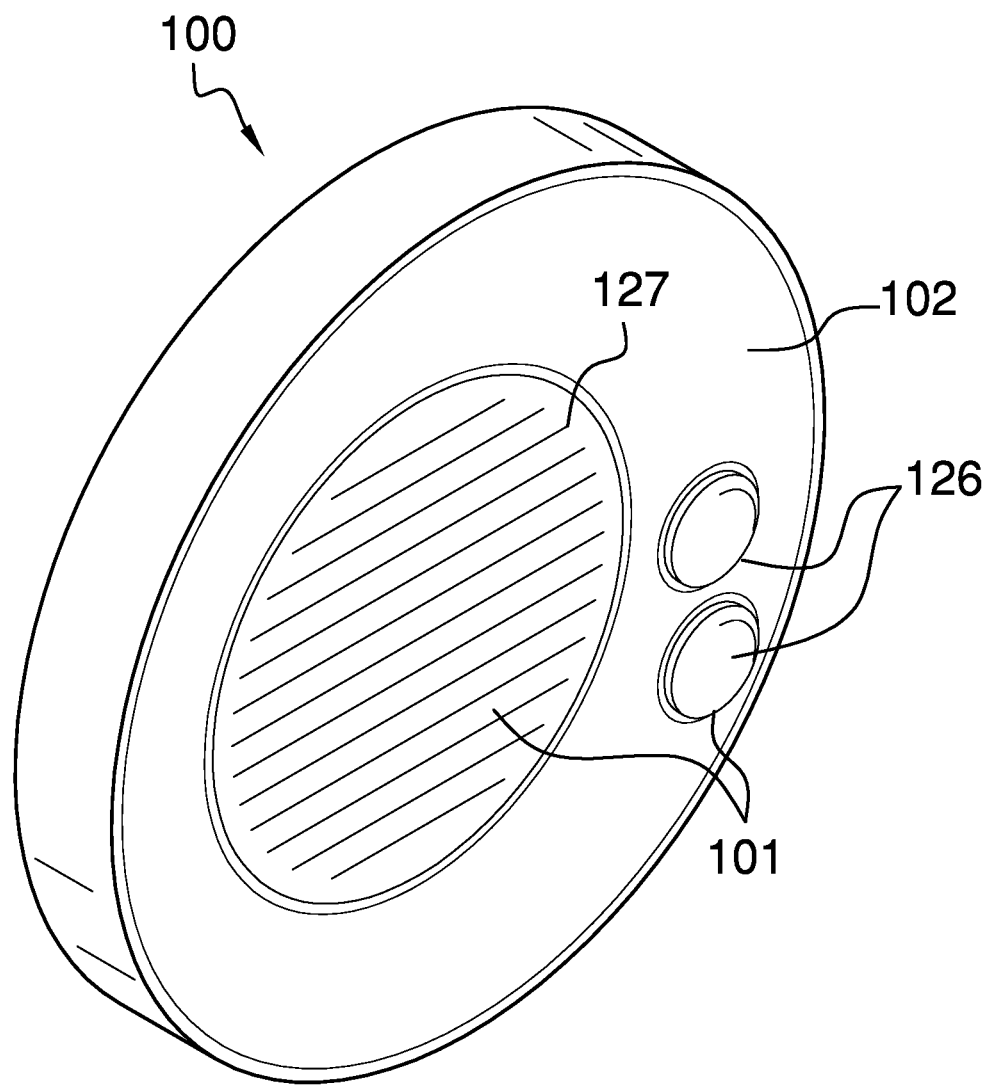
FIG. 1 is a perspective view of an embodiment of the disclosure.
Figure 2:
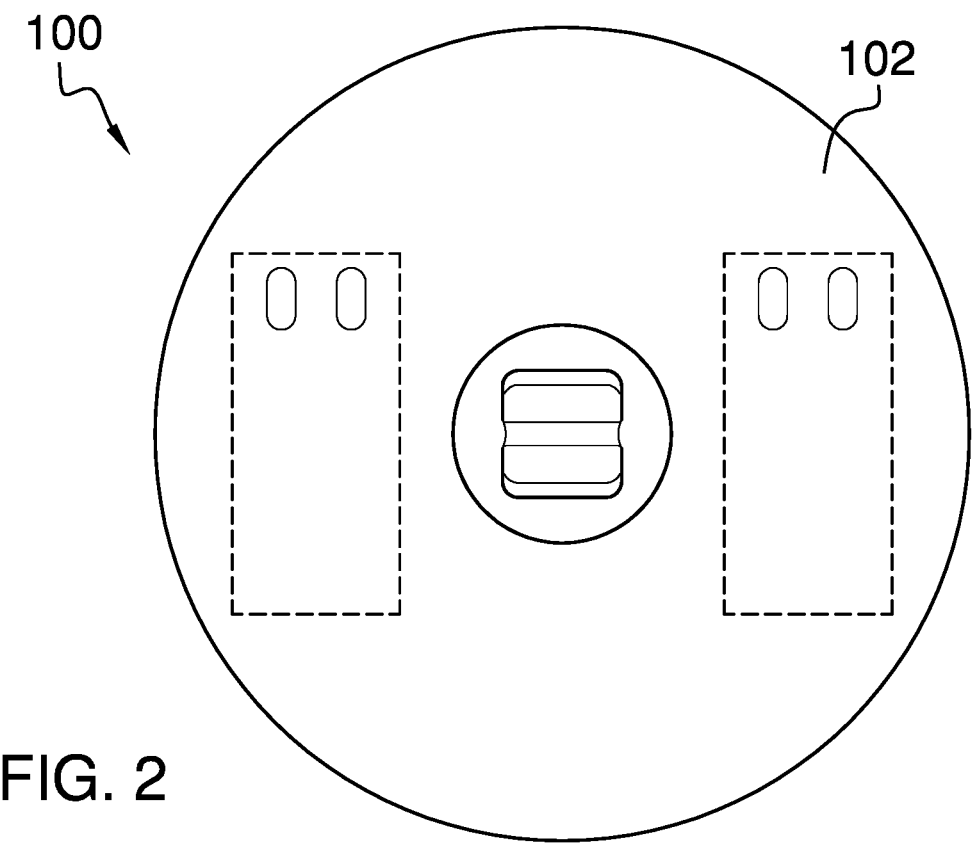
FIG. 2 is a rear view of an embodiment of the disclosure.
Figure 3:
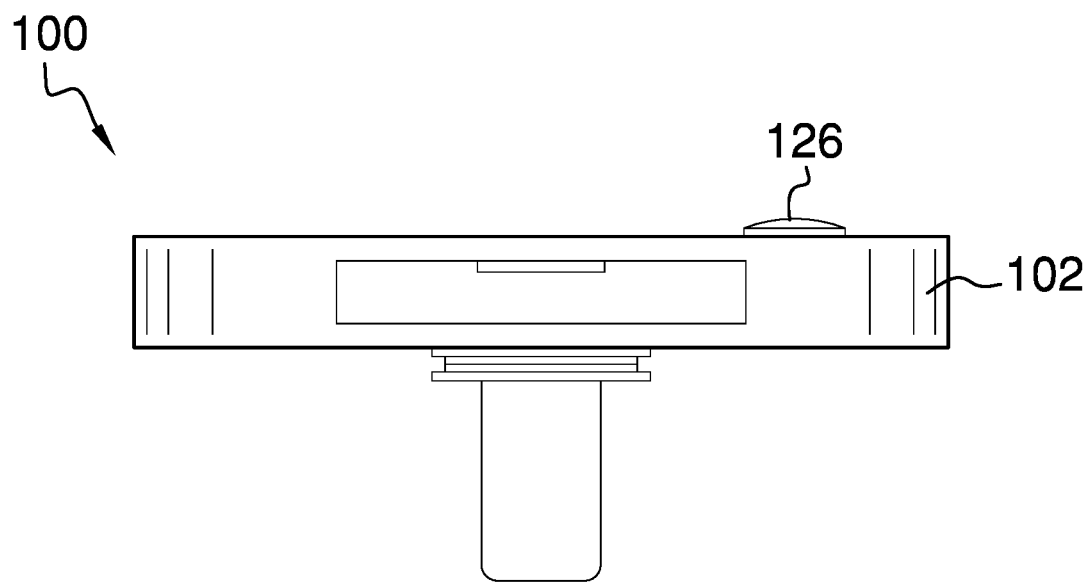
FIG. 3 is a bottom view of an embodiment of the disclosure.
Figure 4:
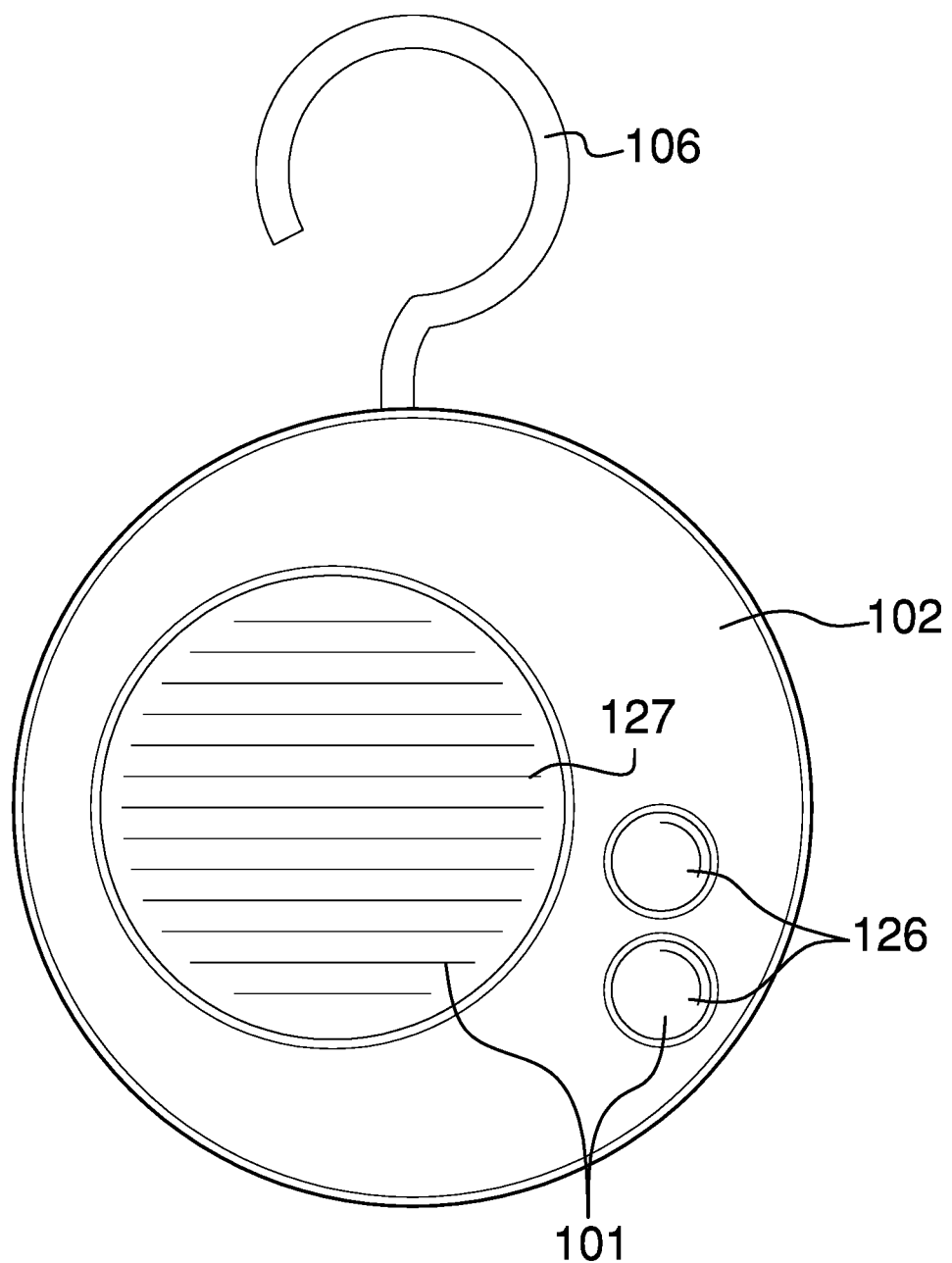
FIG. 4 is a front view of an embodiment of the disclosure.
Figure 5A:
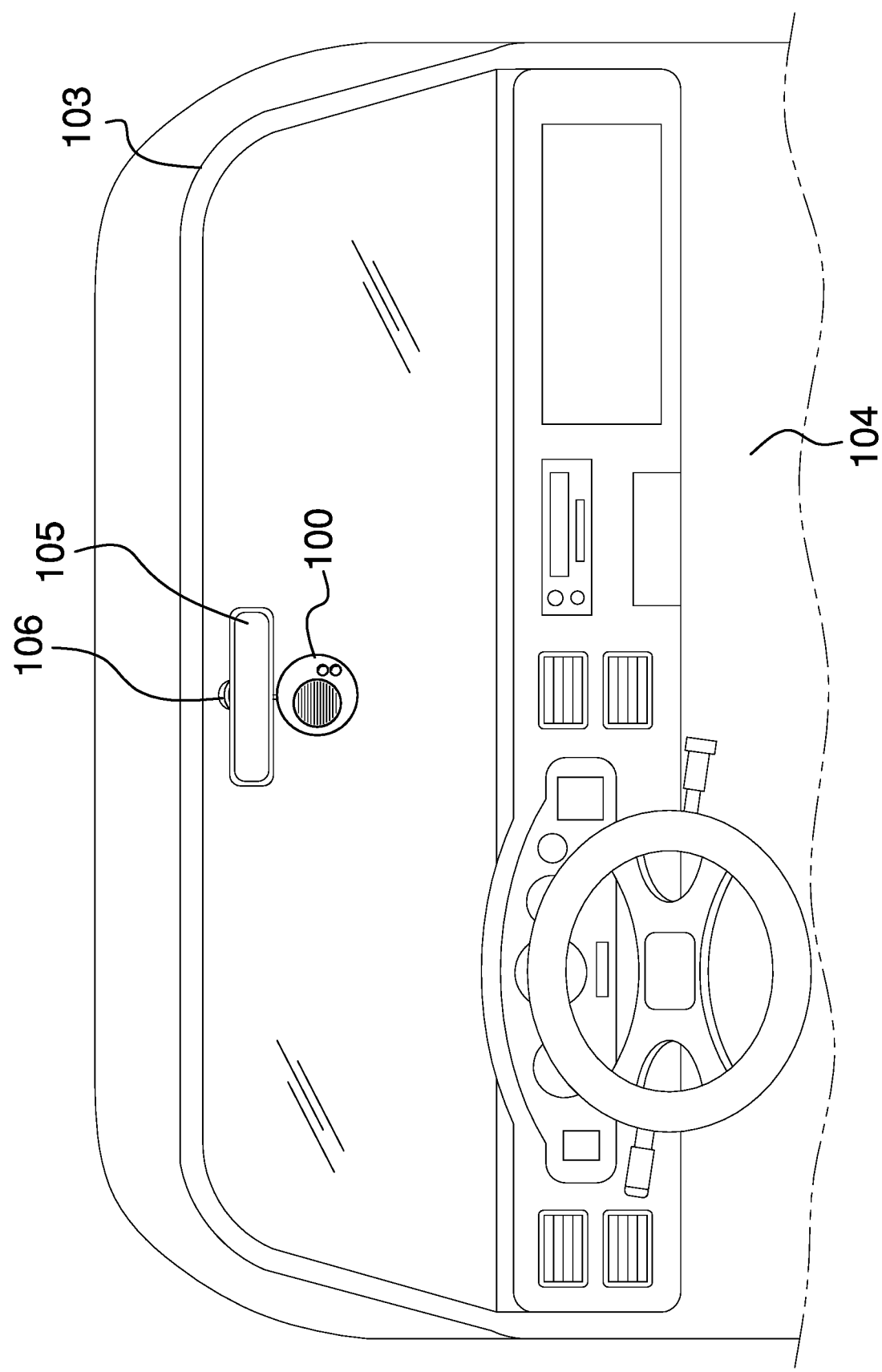
FIG. 5A is an in-use view of an embodiment of the disclosure in a vehicle.
Figure 5B:
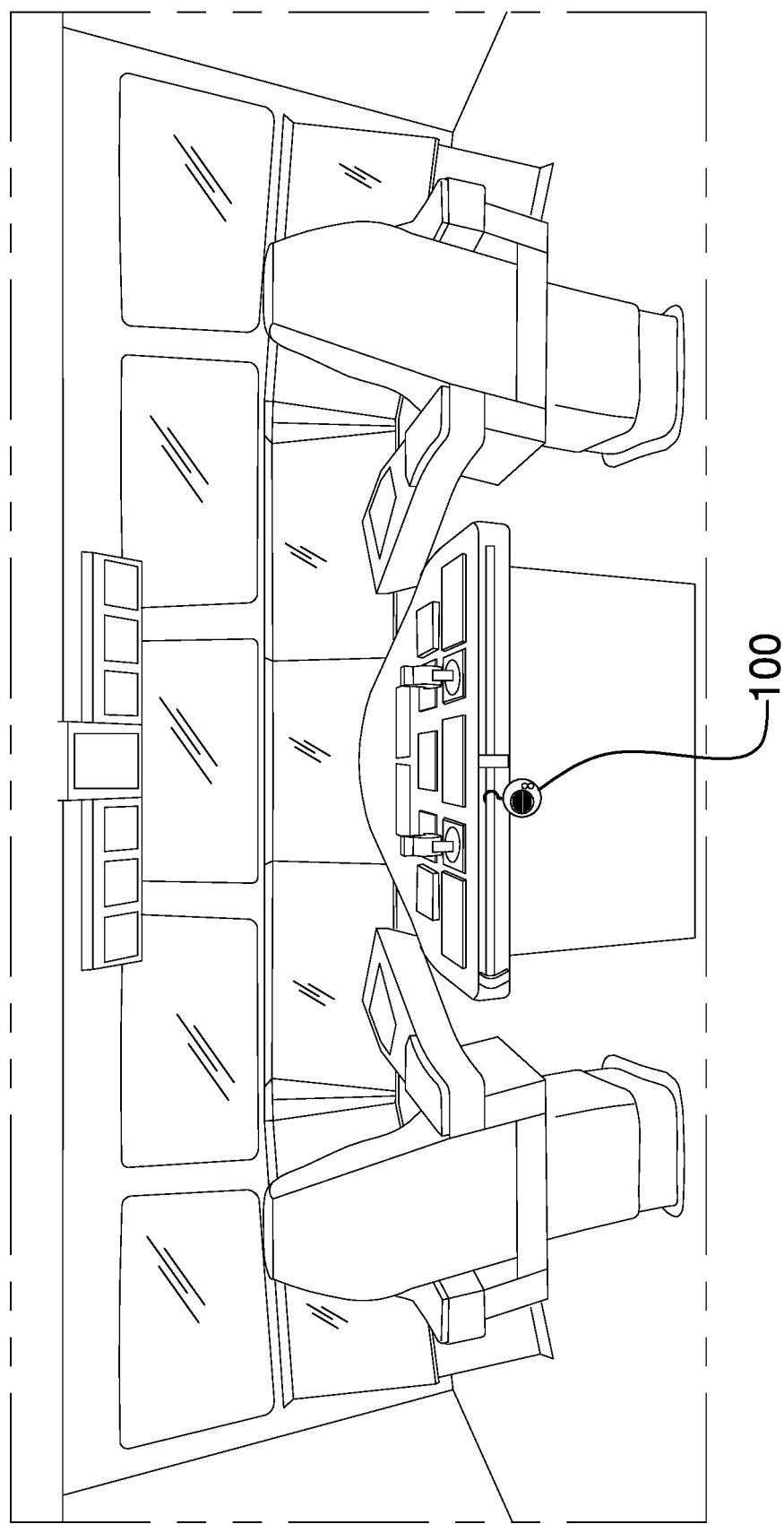
FIG. 5B is another in-use view of an embodiment of the disclosure in a ship.
Figure 6:
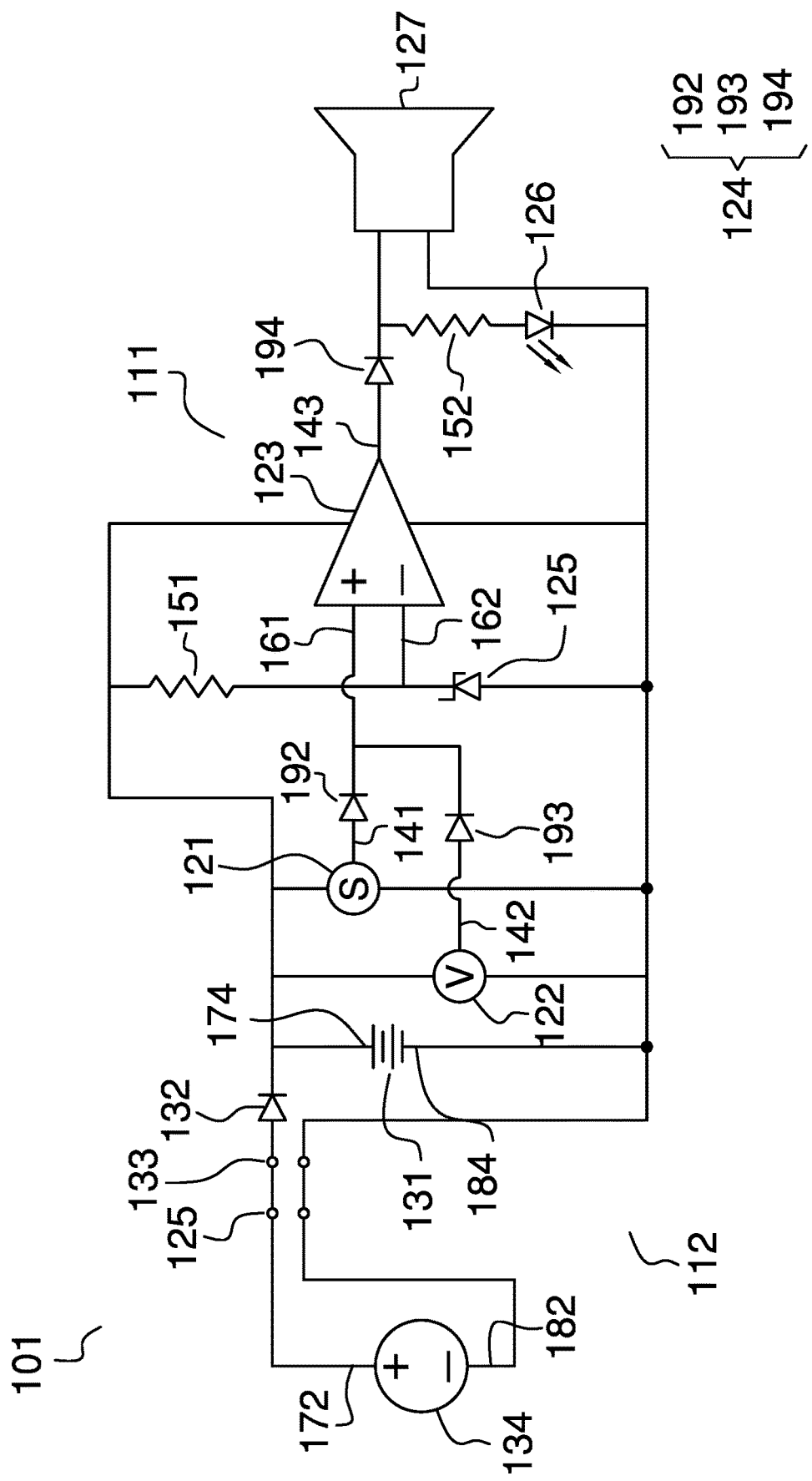
FIG. 6 is a schematic view of an embodiment of the disclosure.
Figure 7:
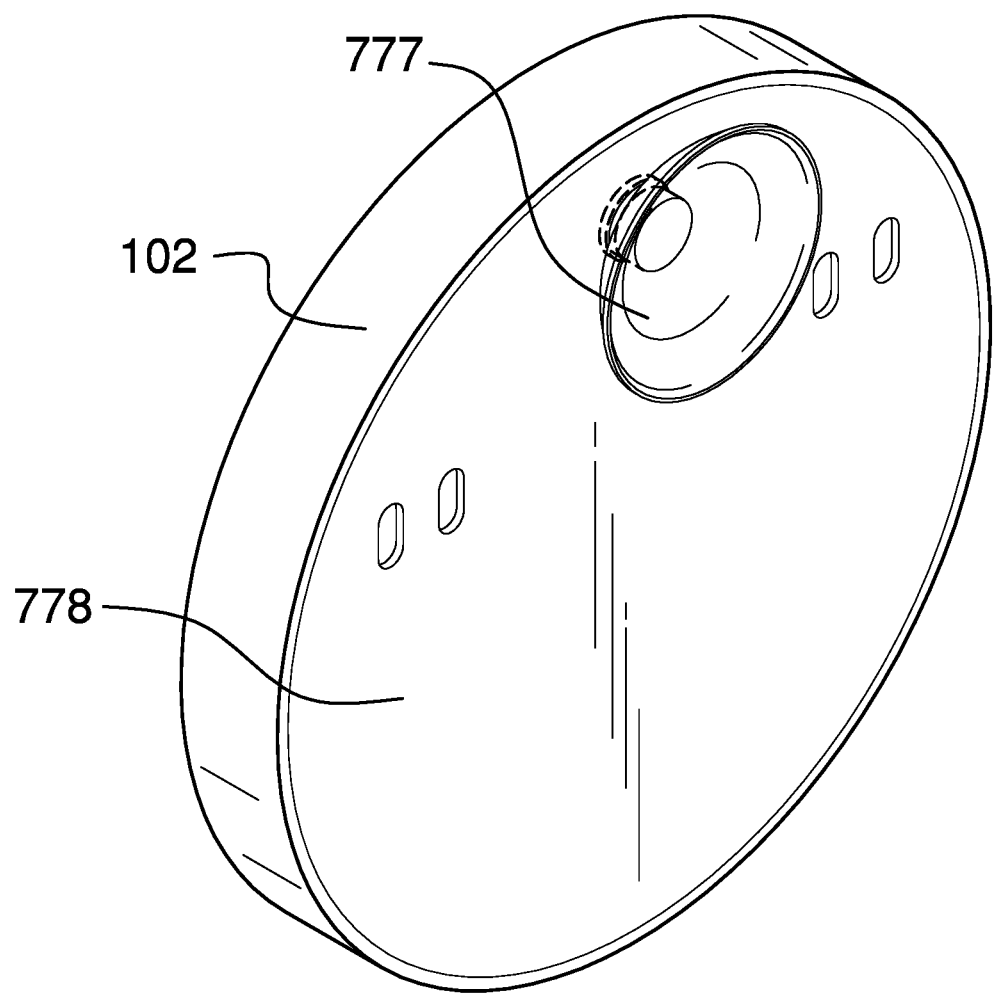
FIG. 7 is a rear view of an embodiment that includes a suction cup.

Detailed reference will now be made to one or more potential embodiments of the disclosure, which are illustrated in FIGS. 1 through 7.

The vehicular carbon monoxide and volatile organic compounds alarm 100 (hereinafter invention) is configured for use with a vehicle 103. The vehicle 103 is further defined with a passenger space 104 and a rearview mirror 105. The invention is maintained in the passenger space 104 of the vehicle 103. The invention 100 is a sensor. The invention 100 monitors the concentration of carbon monoxide and volatile organic compounds in the air in the passenger space 104 of the vehicle 103. The invention 100 generates a visible and audible alarm when the concentration of carbon monoxide and volatile organic compounds in the passenger space 104 of the vehicle 103 exceeds a predetermined level. The invention 100 comprises an operating circuit 101 and a housing 102. The housing 102 contains the operating circuit 101. The housing 102 removably attaches to the rearview mirror 105. Optionally, the housing 102 secures itself to a ceramic or glass surface via a suction cup 777. The suction cup 777 may be provided on a rear surface 778 of the housing 102. The figures depict the housing 102 having a cylindrical shape.

Carbon monoxide is defined in greater detail elsewhere in this disclosure. Volatile organic compounds are defined in greater detail elsewhere in this disclosure. An example of volatile organic compounds would be fuel fumes. The vehicle 103 is defined in greater detail elsewhere in this disclosure. The passenger space 104 is an enclosed space contained in the vehicle 103 used for holding passengers and cargo during transportation. The rearview mirror 105 is a reflective structure that mounts on the windshield of the vehicle 103.

The housing 102 is a rigid structure. The housing 102 contains the operating circuit 101. The housing 102 is formed with all apertures and form factors necessary to allow the housing 102 to accommodate the use, the operation, and the external connections of the operating circuit 101. Methods to form a housing 102 suitable for the purposes described in this disclosure are well-known and documented in the mechanical arts. The housing 102 further comprises a hook 106. The hook 106 is a curved shaft structure that attaches to the housing 102. The hook 106 removably attaches to the rearview mirror 105 such that the rearview mirror 105 suspends the housing 102 in the passenger space 104 of the vehicle 103.

The operating circuit 101 is an electrical circuit. The operating circuit 101 monitors the air in the passenger space 104 of the vehicle 103 for carbon monoxide. The operating circuit 101 generates a visible and an audible alarm when high levels of carbon monoxide are detected. The operating circuit 101 monitors the air in the passenger space 104 of the vehicle 103 for volatile organic compounds. The operating circuit 101 generates a visible and an audible alarm when high levels of volatile organic compounds are detected. The operating circuit 101 is powered independently. By independently powered is meant that the operating circuit 101 can monitor the passenger space 104 of the vehicle 103 for carbon monoxide and volatile organic compounds without an electrical connection to an external power source 134. The operating circuit 101 comprises a sensing circuit 111 and a power circuit 112. The sensing circuit 111 and the power circuit 112 are electrically interconnected.

The sensing circuit 111 is an electrical circuit. The sensing circuit 111 monitors the air in the passenger space 104 of the vehicle 103 for carbon monoxide. The sensing circuit 111 generates a visible and an audible alarm when high levels of carbon monoxide are detected. The sensing circuit 111 monitors the air in the passenger space 104 of the vehicle 103 for volatile organic compounds. The sensing circuit 111 generates a visible and an audible alarm when high levels of volatile organic compounds are detected. The sensing circuit 111 comprises a carbon monoxide sensor 121, a volatile organic compounds sensor 122, an amplifier 123, a plurality of diodes 124, a Zener diode 125, one or more LEDs 126, and a speaker 127.

The carbon monoxide sensor 121 is an electrical device. The carbon monoxide sensor 121 measures the concentration of carbon monoxide in the air in the passenger space 104 of the vehicle 103. The carbon monoxide sensor 121 further comprises a first output signal 141. The first output signal 141 is a voltage that is generated by the carbon monoxide sensor 121. The first output signal 141 is a positive function of the concentration of carbon monoxide in the air in the passenger space 104 of the vehicle 103.

The volatile organic compounds sensor 122 is an electrical device. The volatile organic compounds sensor 122 measures the concentration of volatile organic compounds in the air in the passenger space 104 of the vehicle 103. The volatile organic compounds sensor 122 further comprises a second output signal 142. The second output signal 142 is a voltage that is generated by the volatile organic compounds sensor 122. The second output signal 142 is a positive function of the concentration of volatile organic compounds in the air in the passenger space 104 of the vehicle 103.

Each of the plurality of diodes 124 controls the direction of the current flow through the operating circuit 101. The diode is defined elsewhere in this disclosure. The plurality of diodes 124 further comprises a second diode 192, a third diode 193, and a fourth diode 194.

The second diode 192 installs between the carbon monoxide sensor 121 and the volatile organic compounds sensor 122 such that electric current does not backflow from the second output signal 142 of the volatile organic compounds sensor 122 into the first output signal 141 of the carbon monoxide sensor 121. The third diode 193 is a diode that is wired in series with the second output signal 142 of the volatile organic compounds sensor 122 such that electric current does not backflow from the balance of the sensing circuit 111 into the second output signal 142. The fourth diode 194 is a diode that is wired in series with the third output signal 143 of the amplifier 123 such that electric current does not backflow through the speaker 127 into the amplifier 123.

The Zener diode 125 is an electrical device. The Zener diode 125 presents a reference voltage, known as the Zener voltage, to the amplifier 123 against which the voltage at the first output signal 141 of the carbon monoxide sensor 121 is compared. The Zener diode 125 presents a reference voltage to the amplifier 123 against which the voltage at the second output signal 142 of the volatile organic compounds sensor 122 is compared. The use of a Zener diode 125 for this purpose is well-known and documented in the electrical arts. The Zener diode 125 is defined in greater detail elsewhere in this disclosure. The Zener diode 125 further comprises a first limit resistor 151. The first limit resistor 151 is an electrical device. The first limit resistor 151 electrically connects in series with the Zener diode 125. The first limit resistor 151 limits the amount of electric current flowing through the Zener diode 125.

Each of the one or more LEDs 126 is an electrical device. Each of the one or more LEDs 126 generates visible illumination. Each of the one or more LEDs 126 illuminates when a high concentration of carbon monoxide is detected in the air of the passenger space 104 of the vehicle 103. The one or more LEDs 126 illuminates when a high concentration of volatile organic compounds is detected in the air of the passenger space 104 of the vehicle 103. The one or more LEDs 126 further comprises a second limit resistor 152. The second limit resistor 152 is an electrical device. The second limit resistor 152 electrically connects in series with the one or more LEDs 126. The second limit resistor 152 limits the amount of electric current flowing through the one or more LEDs 126.

The speaker 127 is an electrical device. The speaker 127 is a transducer. The speaker 127 generates an audible sound when a high concentration of carbon monoxide is detected in the air of the passenger space 104 of the vehicle 103. The speaker 127 generates an audible sound when a high concentration of volatile organic compounds is detected in the air of the passenger space 104 of the vehicle 103. In the first potential embodiment of the disclosure, the speaker 127 is a buzzer. The speaker 127 and the buzzer are defined in greater detail elsewhere in this disclosure.

The amplifier 123 is an electrical device. The amplifier 123 is a differential amplifier. The use of a differential amplifier 123 is well-known and documented in the electrical arts. The amplifier 123 further comprises a positive input 161, a negative input 162, and a third output signal 143.

The third output signal 143 is a voltage generated by the amplifier 123. The third output signal 143 provides the electrical energy required to power the speaker 127. The third output signal 143 provides the electrical energy required to power the one or more LEDs 126.

The positive input 161 is an input terminal of the amplifier 123. The positive input 161 electrically connects to the cathode of the second diode 192 such that electric current will flow from the first output signal 141 of the carbon monoxide sensor 121 and through the second diode 192 into the positive input 161. The positive input 161 electrically connects to the cathode of the third diode 193 such that electric current will flow from the second output signal 142 of the volatile organic compounds sensor 122 and through the third diode 193 into the positive input 161.

The negative input 162 is an input terminal of the amplifier 123. The negative input 162 measures the Zener voltage which is the voltage presented between the first limit resistor 151 and the cathode of the Zener diode 125. The second diode 192 is a diode that is wired in series with the first output signal 141 of the carbon monoxide sensor 121 such that electric current does not backflow from the balance of the sensing circuit 111 into the first output signal 141.

The amplifier 123 amplifies the difference between the first output signal 141 of the carbon monoxide sensor 121 and the Zener voltage presented across the Zener diode 125. When the voltage presented at the first output signal 141 of the carbon monoxide sensor 121 is greater than the Zener voltage presented across the Zener diode 125, the amplifier 123 generates a positive voltage at the third output signal 143. The positive voltage at the third output signal 143 forward biases the fourth diode 194 such that an electric current will flow through both the speaker 127 and the one or more LEDs 126 to generate an alarm indicating that high levels of carbon monoxide have been detected.

The amplifier 123 further amplifies the difference between the second output signal 142 of the volatile organic compounds sensor 122 and the Zener voltage presented across the Zener diode 125. When the voltage presented at the second output signal 142 of the volatile organic compounds sensor 122 is greater than the Zener voltage presented across the Zener diode 125, the amplifier 123 generates a positive voltage at the third output signal 143. The positive voltage at the third output signal 143 forward biases the fourth diode 194 such that an electric current will flow through both the speaker 127 and the one or more LEDs 126 to generate an alarm indicating that high levels of volatile organic compounds have been detected.

The third diode 193 installs between the carbon monoxide sensor 121 and the volatile organic compounds sensor 122 such that electric current will not flow from the first output signal 141 of the carbon monoxide sensor 121 into the second output signal 142 of the volatile organic compounds sensor 122.

The power circuit 112 is an electrochemical device. The power circuit 112 is an electrical circuit. The power circuit 112 stores chemical potential energy. The power circuit 112 converts the chemical potential energy into electrical energy used to power the operation of the sensing circuit 111. The power circuit 112 comprises a battery 131, a first diode 132, a charging plug 133, and an external power source 134. The external power source 134 further comprises a charging port 135. The battery 131, the first diode 132, the charging plug 133, the external power 134. and the charging port 135 are electrically interconnected. The battery 131 is further defined with a first positive terminal 171 and a first negative terminal 181. The external power source 134 is further defined with a second positive terminal 172 and a second negative terminal 182.

The battery 131 is an electrochemical device. The battery 131 converts chemical potential energy into the electrical energy used to power the sensing circuit 111. The battery 131 is a commercially available rechargeable battery 131. The chemical energy stored within the rechargeable battery 131 is renewed and restored through the use of the charging plug 133. The charging plug 133 is an electrical circuit that reverses the polarity of the rechargeable battery 131 and provides the energy necessary to reverse the chemical processes that the rechargeable battery 131 initially used to generate the electrical energy. This reversal of the chemical process creates a chemical potential energy that will later be used by the rechargeable battery 131 to generate electricity.

The charging plug 133 forms an electrical connection to an external power source 134 using a charging port 135. The charging port 135 forms a detachable electrical connection with the charging plug 133. The charging plug 133 receives electrical energy from the external power source 134 through the charging port 135. The first diode 132 is an electrical device that allows current to flow in only one direction. The first diode 132 installs between the rechargeable battery 131 and the charging plug 133 such that electricity will not flow from the first positive terminal 171 of the rechargeable battery 131 into the second positive terminal 172 of the external power source 134. In the first potential embodiment of the disclosure, the external power source 134 and the charging port 135 are provisioned through the vehicle 103.

The following definitions were used in this disclosure:

Amplifier: As used in this disclosure, an amplifier refers to an electronic component that increases the voltage, current, or power of an input signal. Specifically, within this disclosure, an amplifier refers to a differential amplifier. A differential amplifier is a device with two inputs with a single output. A differential amplifier amplifies the voltage difference between the two inputs.

Anodes and Cathodes: As used in this disclosure, an anode and a cathode are the connecting terminals of an electrical circuit element or device. Technically, the cathode is the terminal through which the physical electrons flow into the device. The anode is the terminal through which the physical electrons flow out of the device. As a practical matter the anode refers to: 1) the positive terminal of a power consuming electrical circuit element; 2) the negative terminal of a discharging battery or an electrical power source; and, 3) the positive terminal of a charging battery. As a further practical matter the cathode refers to: 1) the negative terminal of a power consuming electrical circuit element; 2) the positive terminal of a discharging battery or an electrical power source; and, 3) the negative terminal of a charging battery. Battery: As used in this disclosure, a battery is a chemical device consisting of one or more cells, in which chemical energy is converted into electricity and used as a source of power. Batteries are commonly defined with a positive terminal and a negative terminal.

Buzzer: As used in this disclosure, a buzzer is two lead electrical device that generates an audible sound when voltage is applied to the two leads.

Carbon Monoxide: As used in this disclosure, carbon monoxide (CAS 630-08-0) refers to a chemical compound with the formula CO.

Cigarette Lighter Plug: As used in this disclosure, a cigarette lighter plug is a standardized electrical connection that attaches an electrically powered device to the electric power system of a vehicle.

Diode: As used in this disclosure, a diode is a two terminal semiconductor device that allows current flow in only one direction. The two terminals are called the anode and the cathode. Electric current is allowed to pass from the anode to the cathode.

External Power Source: As used in this disclosure, an external power source is a source of the energy that is externally provided to enable the operation of the present disclosure. Examples of external power sources include, but are not limited to, electrical power sources and compressed air sources.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Hook: As used in this disclosure, a hook is an object that is curved or bent at an angle such that items can be hung on or caught by the object.

Housing: As used in this disclosure, a housing is a rigid structure that encloses and protects one or more devices.

Inferior: As used in this disclosure, the term inferior refers to a directional reference that is parallel to and in the same direction as the force of gravity when an object is positioned or used normally.

LED: As used in this disclosure, an LED is an acronym for a light emitting diode. A light emitting diode is a diode that is also a light source. Because of close operational correspondence of the function of the cathode and anode of an organic LEDs and the cathode and anode of a semiconductor LED, organic LEDs are included in this definition.

Limit Resistor: As used in this disclosure, a limit resistor is an electrical resistor that is used to limit the flow of electric current through an electrical circuit.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Plug: As used in this disclosure, a plug is an electrical termination that electrically connects a first electrical circuit to a second electrical circuit or a source of electricity. As used in this disclosure, a plug will have two or three metal pins.

Port: As used in this disclosure, a port is an electrical termination that is used to connect a first electrical circuit to a second external electrical circuit. In this disclosure, the port is designed to receive a plug.

Resistor: As used in this disclosure, a resistor is a well-known and commonly available electrical device that presents a resistance that inhibits the flow of electricity through an electric circuit. Within an electric circuit processing alternating currents, the resistor will not affect the phase of the alternating current. A current flowing through a resistor will create a voltage across the terminals of the resistor.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Speaker: As used in this disclosure, a speaker is an electrical transducer that converts an electrical signal into an audible sound.

Suspend: As used in this disclosure, to suspend an object means to support an object such that the inferior end of the object does not form a significant portion of the load path of the object.

Superior: As used in this disclosure, the term superior refers to a directional reference that is parallel to and in the opposite direction of the force of gravity when an object is positioned or used normally.

Transducer: As used in this disclosure, a transducer is a device that converts a physical quantity, such as pressure or brightness into an electrical signal or a device that converts an electrical signal into a physical quantity.

Vehicle: As used in this disclosure, a vehicle is a motorized device used for transporting passengers, goods, or equipment. The term motorized vehicle refers to a vehicle can move under power provided by an electric motor or an internal combustion engine.

Volatile Organic Compounds: As used in this disclosure, volatile organic compounds refer to organic compounds with a relatively low boiling point such that a significant portion of the volatile organic compounds will exist as a gas at normal temperature and pressure. Volatile organic compounds is commonly abbreviated VOC. When measuring volatile organic compounds within the atmosphere, commercially available sensors will generally measure and report all volatile organic compounds as a single aggregated measurement referred to as the total volatile organic compounds. Total volatile organic compounds is commonly abbreviated TVOC.

Windshield: As used in this disclosure, a windshield refers to the front and rear window of a vehicle that is intended to shield the occupants of the vehicle from the wind generated by the normal motion of the vehicle. Windscreen is a synonym for windshield.

Zener Diode: As used in this disclosure, a Zener diode is a two-terminal electrical device that is used to generate a known voltage that is relatively independent variations in the voltage applied to the Zener diode. The known voltage is referred to as the Zener voltage.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A toxic gas alarm comprising
an operating circuit and a housing;
wherein the housing contains the operating circuit;
wherein the toxic gas alarm is configured for use with a vehicle;
wherein the toxic gas alarm is configured to be maintained in a passenger space of the vehicle;
wherein the toxic gas alarm generates a visible and audible alarm when a concentration of carbon monoxide and volatile organic compounds in the passenger space of the vehicle exceeds a predetermined level;
wherein the toxic gas alarm is a sensor;
wherein the toxic gas alarm monitors the concentration of carbon monoxide and volatile organic compounds in the air in the passenger space of the vehicle;
wherein the operating circuit comprises a sensing circuit and a power circuit;
wherein the sensing circuit and the power circuit are electrically interconnected;
wherein the sensing circuit comprises a carbon monoxide sensor, a volatile organic compounds sensor, an amplifier, a plurality of diodes, a Zener diode, one or more LEDs, and a speaker;
wherein the volatile organic compounds sensor, the amplifier, the plurality of diodes, the Zener diode, the one or more LEDs, and the speaker are electrically interconnected;
wherein the plurality of diodes further comprises a second diode, a third diode, and a fourth diode;
wherein the second diode installs between the carbon monoxide sensor and the volatile organic compounds sensor such that electric current does not backflow from the second output signal of the volatile organic compounds sensor into the first output signal of the carbon monoxide sensor;
wherein the third diode is a diode that is wired in series with the second output signal of the volatile organic compounds sensor such that electric current does not backflow from a balance of the sensing circuit into the second output signal;
wherein the fourth diode is a diode that is wired in series with the third output signal of the amplifier such that electric current does not backflow through the speaker into the amplifier.

2. The toxic gas alarm according to claim 1 wherein the housing is a rigid structure;
wherein the housing further comprises a hook;
wherein the hook is a curved shaft structure that attaches to the housing.

3. The toxic gas alarm according to claim 1
wherein the housing is a rigid structure;
wherein the housing further comprises a suction cup;
wherein the suction cup is configured to secure the housing to a ceramic or glass surface;
wherein the suction cup is provided on a rear surface of the housing.

4. The toxic gas alarm according to claim 1 wherein the operating circuit is an electrical circuit.

5. The toxic gas alarm according to claim 4
wherein the operating circuit is powered independently;
wherein by independently powered is meant that the operating circuit can monitor the passenger space of the vehicle for carbon monoxide and volatile organic compounds without an electrical connection to an external power source.

6. The toxic gas alarm according to claim 5
wherein the sensing circuit is an electrical circuit;
wherein the sensing circuit monitors the air in the passenger space of the vehicle for carbon monoxide;
wherein the sensing circuit generates a visible and an audible alarm when high levels of carbon monoxide are detected;
wherein the sensing circuit monitors the air in the passenger space of the vehicle for volatile organic compounds;
wherein the sensing circuit generates a visible and an audible alarm when high levels of volatile organic compounds are detected.

7. The toxic gas alarm according to claim 6
wherein the power circuit is an electrochemical device;
wherein the power circuit is an electrical circuit;
wherein the power circuit stores chemical potential energy;
wherein the power circuit converts the chemical potential energy into electrical energy used to power the operation of the sensing circuit.

8. The toxic gas alarm according to claim 7
wherein the carbon monoxide sensor is an electrical device;
wherein the carbon monoxide sensor measures the concentration of carbon monoxide in the air in the passenger space of the vehicle;
wherein the volatile organic compounds sensor is an electrical device;
wherein the volatile organic compounds sensor measures the concentration of volatile organic compounds in the air in the passenger space of the vehicle.

9. The toxic gas alarm according to claim 8
wherein the carbon monoxide sensor further comprises a first output signal;
wherein the first output signal is a voltage that is generated by the carbon monoxide sensor;
wherein the first output signal is a positive function of the concentration of carbon monoxide in the air in the passenger space of the vehicle;
wherein the volatile organic compounds sensor further comprises a second output signal;
wherein the second output signal is a voltage that is generated by the volatile organic compounds sensor;
wherein the second output signal is a positive function of the concentration of volatile organic compounds in the air in the passenger space of the vehicle.

10. The toxic gas alarm according to claim 9 wherein the Zener diode is an electrical device;
wherein the Zener diode presents a reference voltage to the amplifier;
wherein the reference voltage is a Zener voltage;
wherein the Zener diode further comprises a first limit resistor;
wherein the first limit resistor is an electrical device;
wherein the first limit resistor electrically connects in series with the Zener diode;
wherein the first limit resistor limits the amount of electric current flowing through the Zener diode.

11. The toxic gas alarm according to claim 10
wherein each of the one or more LEDs is an electrical device;
wherein each of the one or more LEDs generates visible illumination;
wherein each of the one or more LEDs illuminates when a high concentration of carbon monoxide is detected in the air of the passenger space of the vehicle;

wherein the one or more LEDs illuminates when a high concentration of volatile organic compounds is detected in the air of the passenger space of the vehicle;
wherein the one or more LEDs further comprises a second limit resistor;
wherein the second limit resistor is an electrical device;
wherein the second limit resistor electrically connects in series with the one or more LEDs;
wherein the second limit resistor limits the amount of electric current flowing through the one or more LEDs;
wherein the speaker is an electrical device;
wherein the speaker is a transducer;
wherein the speaker generates an audible sound when a high concentration of carbon monoxide is detected in the air of the passenger space of the vehicle;
wherein the speaker generates an audible sound when a high concentration of volatile organic compounds is detected in the air of the passenger space of the vehicle.

12. The toxic gas alarm according to claim 11 wherein the amplifier is an electrical device;
wherein the amplifier is a differential amplifier;
wherein the amplifier further comprises a positive input, a negative input, and a third output signal;
wherein the third output signal is a voltage generated by the amplifier;
wherein the third output signal provides an electrical energy required to power the speaker;
wherein the third output signal provides the electrical energy required to power the one or more LEDs;
wherein the positive input is an input terminal of the amplifier;
wherein the negative input is an input terminal of the amplifier.

13. The toxic gas alarm according to claim 12
wherein the positive input electrically connects to the cathode of the second diode such that electric current will flow from the first output signal of the carbon monoxide sensor and through the second diode into the positive input;
wherein the positive input electrically connects to the cathode of the third diode such that electric current will flow from the second output signal of the volatile organic compounds sensor and through the third diode into the positive input;
wherein the negative input measures the Zener voltage which is the voltage presented between the first limit resistor and the cathode of the Zener diode.

14. The toxic gas alarm according to claim 13 wherein the amplifier amplifies a difference between the first output signal of the carbon monoxide sensor and the Zener voltage presented across the Zener diode;
wherein when the voltage presented at the first output signal of the carbon monoxide sensor is greater than the Zener voltage presented across the Zener diode, the amplifier generates a positive voltage at the third output signal;
wherein the amplifier further amplifies a difference between the second output signal of the volatile organic compounds sensor and the Zener voltage presented across the Zener diode;
wherein when the voltage presented at the second output signal of the volatile organic compounds sensor is greater than the Zener voltage presented across the Zener diode, the amplifier generates a positive voltage at the third output signal.

15. The toxic gas alarm according to claim 14 wherein the positive voltage at the third output signal forward biases the fourth diode such that an electric current will flow through both the speaker and the one or more LEDs to generate an alarm indicating that high levels of carbon monoxide have been detected.

16. The toxic gas alarm according to claim 15
wherein the power circuit comprises a battery, a first diode, a charging plug, and the external power source;
wherein the external power source further comprises a charging port;
wherein the battery, the first diode, the charging plug, the external power source, and the charging port are electrically interconnected;
wherein the battery is further defined with a first positive terminal and a first negative terminal;
wherein the external power source is further defined with a second positive terminal and a second negative terminal.

17. The toxic gas alarm according to claim 16
wherein the battery is an electrochemical device;
wherein the battery is a rechargeable battery;
wherein the charging plug is an electrical circuit that reverses the polarity of the rechargeable battery and provides the energy necessary to reverse the chemical processes that the rechargeable battery initially used to generate the electrical energy;
wherein the charging plug forms an electrical connection to an external power source using a charging port;
wherein the charging port forms a detachable electrical connection with the charging plug;
wherein the first diode is an electrical device that allows current to flow in only one direction;
wherein the first diode installs between the rechargeable battery and the charging plug such that electricity will not flow from the first positive terminal of the rechargeable battery into the second positive terminal of the external power source.

* * * * *